United States Patent [19]

Rudy et al.

[11] Patent Number: 4,526,177

[45] Date of Patent: Jul. 2, 1985

[54] ELECTRONIC ANATOMICAL PROBE

[76] Inventors: Michael A. Rudy, 619 French Rd., Rochester, N.Y. 14618; Joseph Jacob, 42 White Ter., Ramsey, N.J. 07446

[21] Appl. No.: 507,358

[22] Filed: Jun. 24, 1983

[51] Int. Cl.³ .............................................. A61B 5/06
[52] U.S. Cl. .................................... 128/737; 324/236
[58] Field of Search ........................ 128/737, 653–654, 128/1.3–1.5; 324/236

[56] References Cited

U.S. PATENT DOCUMENTS

| | | | |
|---|---|---|---|
| 2,129,058 | 9/1938 | Hedden | 128/737 X |
| 2,321,355 | 6/1943 | Berman | 128/1.4 |
| 2,321,356 | 6/1943 | Berman | 128/1.4 |
| 2,393,717 | 1/1946 | Speaker | 128/737 X |
| 2,442,805 | 6/1948 | Gilson | 128/737 X |
| 3,209,245 | 9/1965 | Hauge | 324/239 |
| 3,381,217 | 4/1968 | Williamson et al. | 324/236 |
| 3,460,528 | 8/1969 | Carney | 128/737 X |
| 3,546,628 | 12/1970 | Zitter | 331/117 |
| 4,068,189 | 1/1978 | Wilson | 331/65 |
| 4,230,987 | 10/1980 | Mordwinkin | 324/236 |

FOREIGN PATENT DOCUMENTS 2842203  4/1980  Fed. Rep. of Germany ...... 128/737

Primary Examiner—Lee S. Cohen
Assistant Examiner—Angela D. Sykes
Attorney, Agent, or Firm—Shlesinger, Fitzsimmons & Shlesinger

[57] ABSTRACT

A wire sensing coil is sealed in the tip of an elongate, rigid, plastic probe, and is connected by a coaxial cable releasably to a housing containing a fixed frequency, crystal-controlled oscillator, the output of which is applied through a high impedance resistor and the cable to the coil. The number of turns in the coil and the cable length are carefully selected so that the coil remains tuned to the frequency of the oscillator, except when the tip of the probe approaches a metal object, at which time the voltage drop across the coil decreases. The housing also contains an audible alarm, and a sensing circuit which detects the voltage drop across the coil, and which energizes the alarm when the voltage across the coil drops below a preset or predetermined level. The housing also contains a rechargable battery for supplying power to the oscillator and alarm circuits, and a recharging circuit for recharging the battery. A manually operable switch on the housing connects the battery to the oscillator when the switch is in its ON position, and connects the recharging circuit to the battery when in its OFF position.

20 Claims, 4 Drawing Figures

ELECTRONIC ANATOMICAL PROBE

BACKGROUND OF THE INVENTION

This invention relates to an electronic detector for locating metallic objects in a human or animal body, and more particularly to a hand manipulated probe for use by surgeons and the like for locating metal objects hidden from view within a wound or surgical opening.

One of the major difficulties encountered by surgeons, medical examiners, veterinarians, and the like, is the location of foreign objects which have entered a body or carcass as a result of a wound or surgical procedure. More often than not such objects are metallic (bullets, broken scalpel blades, surgical needles, metallic fragments, etc.), and because of the particular manner in which they entered the body their exact locations cannot be determined simply by observation. In many instances, even when multiple X-Ray studies can demonstrate the location of metallic foreign objects, physically locating, grasping, and removing these foreign objects can be extremely difficult because of limited visibility, limited usability of tactile sensations, and limited range of motion of surgical instruments within certain areas of the body. Moreover, in many cases the urgency of the situation rules out the use of any time-consuming procedures for locating the foreign objects. Consequently there is a critical need for an instrument which can be used quickly and relatively simply to locate foreign metal particles in a wound, surgical opening, or the like.

For example, when a bullet enters a person's body at high speed, it may be deflected several times along different paths once it has entered the body, thus making it extremely difficult to determine where it finally came to rest. For that matter fragments of such an object might be located in different parts of the body, and if not completely removed during a surgical procedure could result in malpractice litigation against the surgeon who was responsible for removing the bullet. Surgeons also face the threat of litigation resulting from the accidental loss of surgical needles in a patient's body or accidental breakage and loss of metal instruments (e.g., the tip of a scalpel blade) during a surgical procedure. It is therefore of primary importance that an instrument be provided which will enable a surgeon rapidly and accurately to detect small metal objects in wounds or surgical openings.

Heretofore efforts have been made to provide metal detecting instruments of the type described and typically such instruments have included an electric coil wound within a probe which can be inserted into an incision or wound. For example, U.S. Pat. Nos. 2,393,717 and 2,442,805 disclose instruments of the type in which the tank coil of one of two oscillators is located in the probe. The outputs of the two oscillators are mixed, amplified, and applied to a speaker, or the like, which under normal conditions produces a low frequency beat note. However, when the probe coil approaches a metallic object in a wound or the like, its inductance is changed and causes an audible and unmistakable change in the normal beat frequency to occur, thereby to denote the presence of the metal object.

In the case of U.S. Pat. Nos. 2,321,355 and 2,321,356, one or more probe coils are connected remote from the probe to corresponding balancing coils. When the circuit is energized, the probe coils create around the outside of the probe a field which, when placed in the vicinity of a metal object in a wound, creates an imbalance in the circuit, and thereby triggers an indicator to denote the presence of the object.

Although not concerned with surgical probes, U.S. Pat. No. 3,546,628 discloses a metal detector of the eddy current killed oscillator variety. In this device the detecting coil is the tank coil of an oscillating tank circuit. The oscillator circuit normally is tuned at a high frequency above the audible range, but when the tank coil is detuned by placing the probe near a metal object, the frequency of the output signal drops to an audible range. U.S. Pat. No. 3,381,217 discloses a device for detecting metal particles in fruit, tobacco, and the like, by using the tank coil of an oscillator to detect metal particles in a manner similar to that described above. However, the device is designed to be fixed in a stationary position adjacent a moving conveyor which advances the fruit or tobacco past the detector.

Other types of detectors are disclosed in U.S. Pat. Nos. 3,460,528, 3,209,245 and 4,068,189, but appear to be less pertinent to this invention than those discussed above.

One of the major disadvantages of prior such probes is that their respective balancing circuits require very careful adjustment each time that the associated instrument is to be employed. In an operating room, for example, if the device is powered by a conventional AC power supply, it must be frequently adjusted to compensate for fluctuations in the voltage supply. In those cases where the detection device utilizes a pair of oscillators to develop a beat frequency, ambient temperature changes also affect the tuning of the reference oscillator and therefore require its adjustment prior to using the instrument. Moreover, since the search coils employed in such prior devices are frequently subjected to shock loading during handling, the tuning of the associated detector circuit frequently must be adjusted to compensate for such disturbances.

The very size of such prior detectors has also been a disadvantage, particularly in those cases where time is of the essence, as for example in the emergency room of a hospital where the need for handling bulk equipment could interfere with proper care of a patient. For the same reasons, the patient's care would be neglected if it were necessary to take the time to calibrate or properly adjust a detector of the type described, prior to being able to use it on a patient.

It is therefore an object of this invention to provide an improved anatomical probe or detector of the type described which is substantially more compact and reliable than prior such probes.

A more specific object of this invention is to provide an improved anatomical probe of the type described which does not have to be tuned or adjusted each time prior to its use on a patient or the like.

A further object of this invention is to provide a small, portable, battery-operated anatomical probe or detector which ideally is tuned only once during its manufacture, and thereafter need not to be readjusted prior to its use, during use, or even after repeated use.

Other objects of the invention will be apparent hereinafter from the specification and from the recital of the appended claims, particularly when read in conjunction with the accompanying drawings.

SUMMARY OF THE INVENTION

A wire sensing coil is wound about a small, cylindrical ferrite core, which is sealed by a non-toxic, completely polymerized polymeric substance, such as an epoxy resin, in the outer end or tip of a tubular probe, which is about the size of a conventional pencil. The coil ends are attached in the probe to one end of an elongate (e.g. six feet) coaxial cable, which is releasably attached at its opposite end to a housing containing a crystal controlled, solid state oscillator. The output of the oscillator is connected through a high impedance element, such as a resistor, to one side of the coil, the opposite side of which is grounded.

The oscillator is powered by a rechargable battery, such as a nickel-cadmium battery, and when energized rings or shock excites the sensing coil at a high frequency in a manner similar to the tank coil of an oscillator. At time of manufacture the probe, coil and coaxial cable are carefully tuned to the resonant frequency of the oscillator so that the voltage drop across the coil remains constant until such time that the coil is placed in the proximity of a metal object. When this occurs, the resultant change in the coil inductance lowers the voltage drop across the coil. This voltage drop is sensed by a comparator circuit in the housing, the output of which then energizes both an indicator lamp on the housing and an audible warning device located in the housing.

Also mounted on the housing is a manually-operable ON-OFF switch for selectively connecting the battery to the oscillator and detecting circuit. The housing contains a recharging circuit and sockets for releasably connecting the recharging circuit to an A.C. power supply.

THE DRAWINGS

DETAILED DESCRIPTION OF THE PREFERRED EMBODIMENTS

Figure 1:
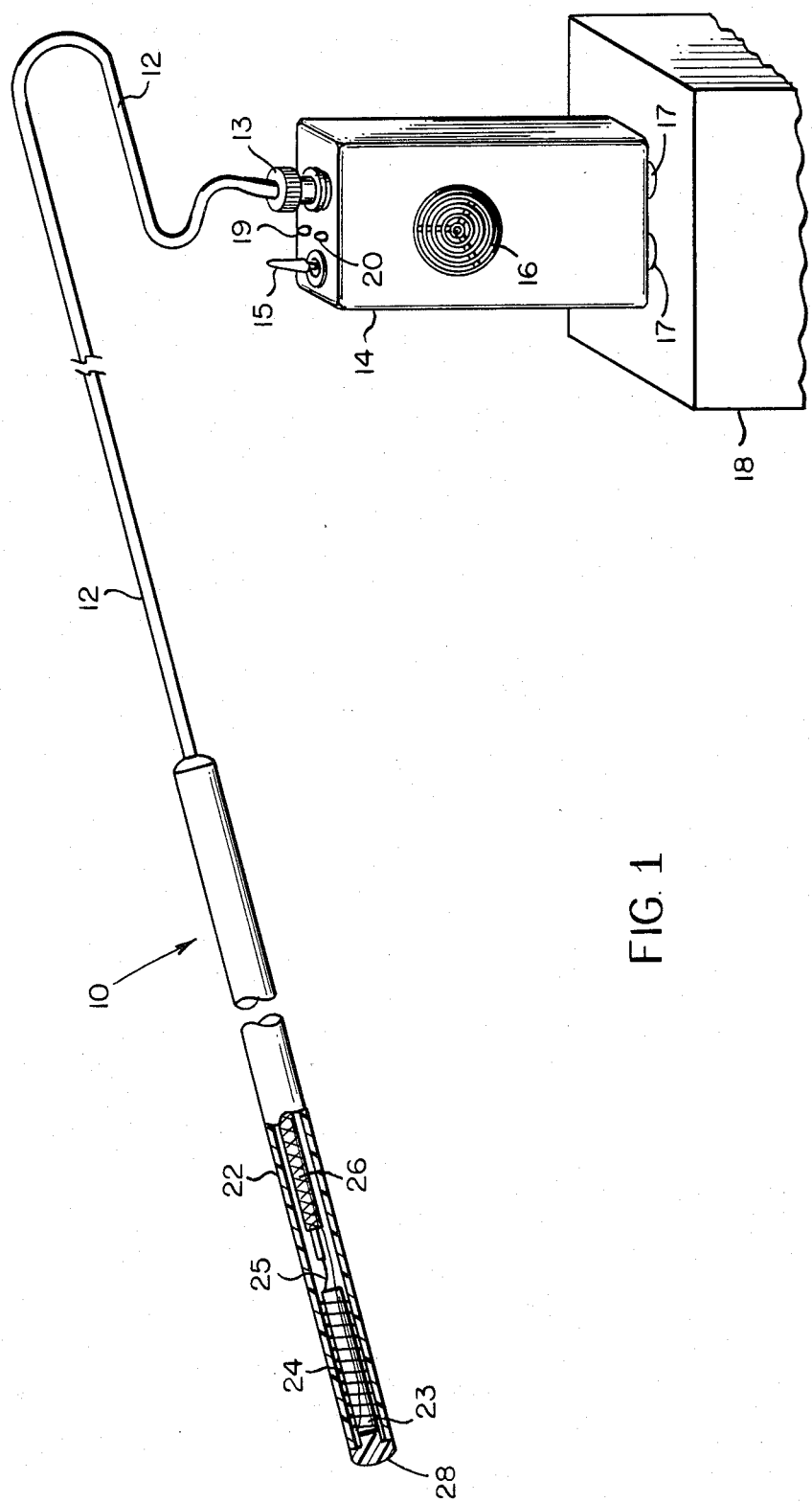
FIG. 1 is a fragmentary elevational view of a metal detecting device made according to one embodiment of this invention, including a manually manipulable probe releasably connected by a coaxial cable to a housing which contains a battery-operated circuit for powering the probe, the housing being shown releasably mounted on a battery charging device.

Referring now to the drawings by numerals of reference, and first to FIG. 1, 10 denotes generally an elongate, rigid probe, which at one end is connected by a coaxial cable 12 and conventional connector 13 with the upper end of a rectangularly shaped housing 14, which contains the hereinafter described battery operated circuit that powers the probe. Projecting form the upper end of housing 14 is a manually operable ON-OFF switch 15, which controls the supply of power to the probe 10. In one sidewall thereof housing 14 contains a screened opening 16, which is disposed to register with an audible alarm device that is mounted in housing 14 as noted hereinafter.

Housing 14 has in its lower end a pair of spaced socket elements 17 of conventional design, which are employed for releasably mounting the housing on the upper end of a battery charging stand 18. This stand, as noted in greater detail hereinafter, contains a transformer for use in recharging the battery in housing 14. Also projecting from the upper surface of housing 14 adjacent the switch 15 are red and green lamp elements 19 and 20, respectively, one of which (element 19) is adapted to be illuminated when the switch 15 is in its ON position, and the other of which (20) is adapted to be illuminated when the probe detects the presence of a metallic object.

The probe 10 comprises an elongate, rigid tube 22 made from a plastic material such as a phenolic resin or the like, and which may be coated with a fluid impervious plastic that is acceptable for use within the human body. Cable 12 extends into one end of tube 22 (the right end thereof as shown in FIG. 1) to a point adjacent a counterbore which is formed in the opposite end or tip of the tube. Mounted in the counterbore end of tube 22 is a cylindrical, ferrite core 23. Wound around the outside of core 23 within tube 22 is a wire coil 24, one end of which is connected to the central conductor or core wire 25 in cable 12, and the other end of which is connected to the shield 26 of the cable to be grounded thereby. As noted in greater detail hereinafter, cable 12 is glued or otherwise secured against movement in tube 22; and the tip end of the tube is filled and sealed with a non-toxic, completely polymerized polymeric substance, such as an epoxy resin or the like, which forms a cap or plug 28 that secures the core 23 and its winding against movement in the tube 22.

Figure 2:
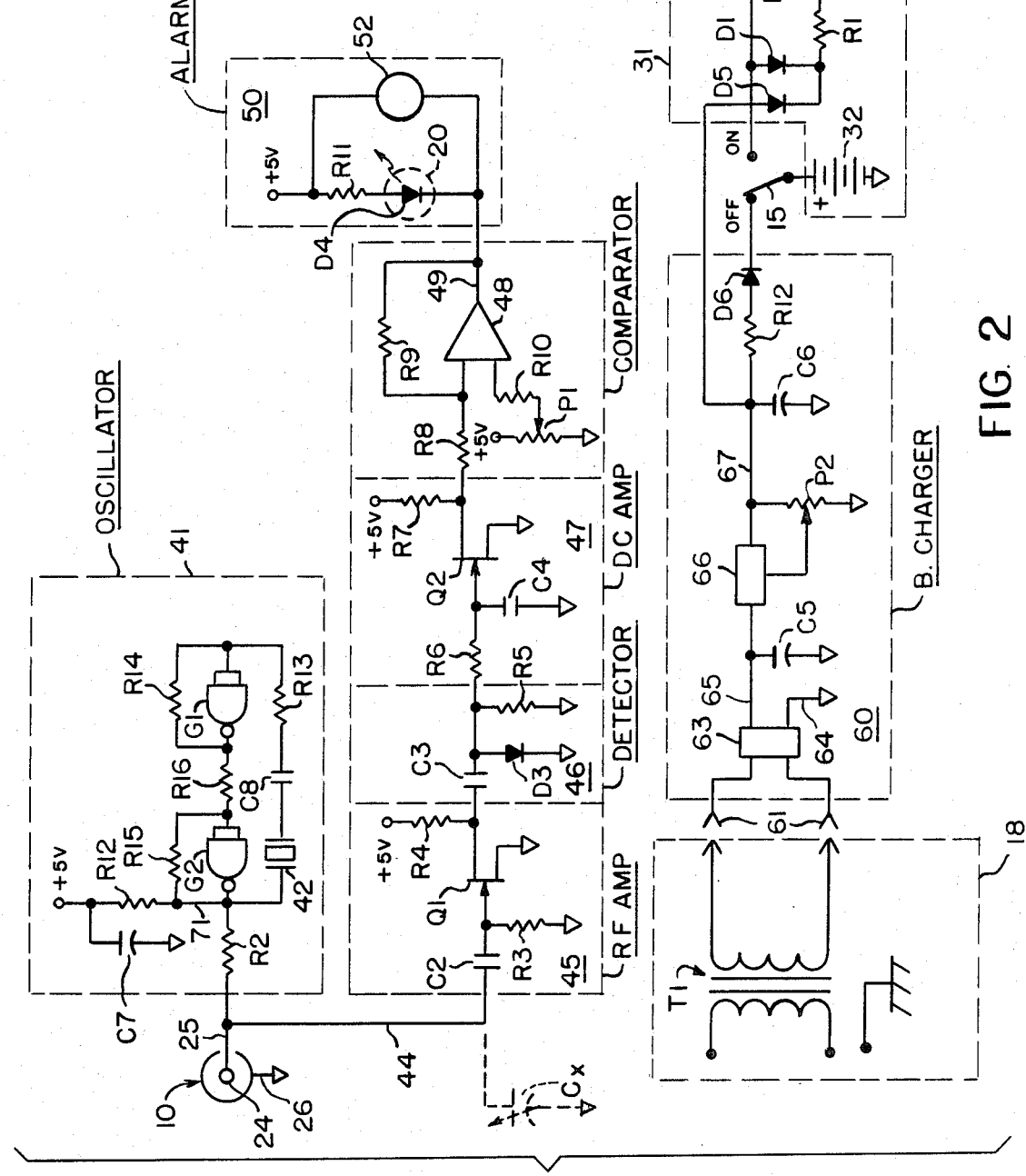
FIG. 2 is a wiring diagram illustrating schematically one manner in which the device can be wired for operation.

As shown more clearly in FIG. 2, housing 14 contains a DC power supply 31 comprising, for example, a nine-volt nickel-cadium battery 32 the positive terminal of which is connected by the switch 15 selectively to an ON or an OFF terminal. When switch 15 is engaged with the ON terminal the output of battery 32 is applied to a voltage regulator 34, the output of which is connected through a capacitor C1 to ground, and to a power supply terminal 36 to maintain the terminal at approximately five volts. Also at this time the output of battery 32 is applied through a diode D1, a resistor R1 and a light-emitting diode D2 to ground. As shown by broken lines in FIG. 2, diode D2 registers with the lamp element 19 in the top of housing 14 to illuminate the latter whenever the output of battery 32 is connected to terminal 36.

Terminal 36 supplies the voltage for powering a fixed frequency oscillator 41, which includes in its circuit a piezoelectric crystal 42 for stablizing its output frequency as described in more detail hereinafter. The output of oscillator 41 is connected through a high impedance resistor R2 (for example one megohm) to the core conductor 25 of the coaxial cable 12. The result is that a high frequency signal or pulse is applied by the oscillator 41 intermittently to the probe coil 24, thereby causing the probe to ring at the driving frequency of the oscillator. Moreover, as noted in greater detail hereinafter, the probe 10, the cable 12 and its connector 13 are carefully selected and assembled so that they are tuned to resonate at the oscillator frequency, and therefore do not require any further adjustment in the field. As a consequence, when the probe is operating and its sensing coil 24 is not near a metallic object, the voltage drop across coil 24 remains a constant, predetermined value.

However, if during use the tip of the probe approaches a metallic object, the field generated by coil 24 around the tip of the probe will create eddy currents in the object which in turn will alter the inductance of coil 24 in such manner that the voltage across the coil will drop. As shown in FIG. 2, this voltage drop is sensed by a conductor 44, which is connected at one end between the resistor R2 and the wire 25, and at its opposite end to one side of a capacitor C2, which forms the input to an RF amplifier noted in FIG. 2 by the numeral 45. At its opposite side C2 is connected through another high impedance resistor R3 to ground, and to the gate terminal of a field effect transistor Q1, which also forms part of the amplifier 45. The source terminal of this transistor is connected to ground, while its drain terminal is connected through a resistor R4 to the five volt power supply, and also to one side of a capacitor C3, which forms the input to a detector stage 46. At its opposite side capacitor C3 is connected to ground through a diode D3 and a resistor R5, which is in parallel in diode D3.

This opposite side of capacitor C3 is also connected to one side of the resistor R6, the opposite side of which is connected through a capacitor C4 to ground, and to the gate terminal of another field effect transistor Q2, which forms part of a direct current amplifier 47. The souce terminal of transistor Q2 is connected to ground, and its drain terminal is connected through a resistor R7 to the five volt power supply, and to one side of a resistor R8. At its opposite side resistor R8 is connected to one input of a DC voltage comparator 48, and through a resistor R9 to the output 49 of the comparator. The other input of comparator 48 is connected through a resistor R10 to a potentiometer P1, which can be adjusted to set the reference voltage which must be applied through resistor R8 to the first-named input of the comparator in order to maintain a predetermined signal level at its output 49.

The output 49 of comparator 48 is designed to control the energization of an alarm device 50, comprising a conventional audio signaling device 52, which is connected at one side to a comparator output 49 and at its oppsite side to the five volt power supply. This signal device 52, which may be of the type sold under the trademark "Sonalert", is positioned in housing 14 so that it registers with the screened opening 16, whereby when it is energized its high frequency output signal will be clearly audible through the housing opening 16. Connected in series with each other and in parallel with the audio device 52 are another resistor R11, and a light-emitting diode D4 which registers with the lamp element 20. Diode D4 is energized simultaneously with the audio device 52 whenever the probe 10 senses a metallic object, thus to provide a visual indication of its presence as well as the audible signal provided by the device 52.

As noted above, the battery 32 is of the rechargeable variety. For this reason housing 14 contains a battery charging circuit denoted generally in FIG. 2 by the numeral 60, and comprising a pair of banana connectors 61 located in the sockets 17 at the bottom of the housing, and connected to the input of a rectifier 63, which is fixed on a circuit board in the housing. One of the outputs of rectifier 63 is grounded at 64 and the other output 65 is connected through a capacitor C5 to ground, and to the input of a voltage regulator 66. One output of regulator 66 is connected through a potentiometer P2 to ground, and the other output, the value of which is controlled by the pot P2, is applied by a conductor 67 through a capacitor C6 to ground, and through a diode D5 and the resistor R1 to the diode D2 which registers with the lamp element 19. The conductor 67 is also connected through a resistor R12 and a diode D6 with the OFF contact of the switch 15.

The banana connectors 61 are adapted releasably to be attached by mating connectors in the battery charging stand 18 with the secondary coil of a step-down transformer T1 of conventional design, which is mounted in the stand 18 to supply an AC input of approximately 12 volts to the rectifier 63. When the connectors 61 are plugged into the stand 18 and switch 15 is engaged with its OFF contact (as shown in FIG. 2), the voltage regulator 66 can produce on line 67 a recharging voltage which is supplied to the positive terminal of battery 32, and in an amount determined by the setting of the pot P2. The same voltage is applied through the diode D5 and the resistor R1 to the diode D2, which therefore illuminates the red lamp element 19 to indicate to an observer that the battery charging circuit is active, and that the battery is being recharged.

Obviously when the housing 14 is removed from stand 18 the battery charging circuit is automatically deenergized. The diode D6 and the resistor R12 prevent any DC voltage from the battery from causing current flow in the reverse direction through the battery charging circuit.

Referring again to oscillator 41, the five volt power supply for the crystal 42 is connected through a capacitor C7 to ground, and a resistor R12 and a line 71 to one side of crystal 42. Crystal 42 is connected in series with a capacitor C8 and resistor R13, and in parallel with a pair of 2-input positive NAND gates G1 and G2, which form part of an integrated circuit commonly identified as an IC 7400 of the dual-in-line variety; and which is adapted to be powered from the five volt supply in a conventional manner (not illustrated). These gates form part of a feed back circuit including resistors R14 and R15 connected across gates G1 and G2, respectively, and in series with a resistor R16 connected between the output of gate G1 and the input of gate G2.

In the embodiment illustrated in FIGS. 1 and 2, and merely by way of example, the cable 12 is approximately six feet in length; the tube 22 is approximately six inches long and has a ¼ inch OD and a ⅛ inch ID; and coil 24 comprises approximately seventy-five turns of wire. Sample values for the capacitors and resistors disclosed in FIG. 2 are as follows:

| Capacitors | |
|---|---|
| C1 - 22 μfd | C5 - 22 μfd |
| C2 - .05 μfd | C6 - .47 μfd |
| C3 - .05 μfd | C7 - .47 μfd |
| C4 - .05 μfd | C8 - 15 pfd |

| Resistors (Ω) | | |
|---|---|---|
| R1 - 1K | R6 - 1 Meg | R11 - 1K |
| R2 - 1 Meg | R7 - 1.8K | R12 - 5.6K |
| R3 - 1 Meg | R8 - 10K | R13 - 270 |
| R4 - 1K | R9 - 10 Meg | R14 - 580 |
| R5 - 4.7 Meg | R10 - 10K | R15 - 1.8K |
| | | R16 - 240 |

As noted above, one of the features of the invention is the fact that the probe 10 and its associated coaxial cable 12 and connector 13 are designed at the time of manufacture to be tuned to the frequency of the signal output of the oscillator 41. In this connection these elements form an assembly which functions as the tank circuit of the oscillator, and once they have been tuned to the oscillator frequency, the pot P1 can be adjusted to require that the alarm device 50 be deenergized until such time that the voltage drop across the sensing coil 24 is lowered or diminished by a predetermiend value. In the embodiment illustrated, once this voltage has dropped below a predetermined value the output 49 of the comparator 48 drops to a value that permits the alarm device 50 to be energized, and to remain energized until the drop across probe 24 once again increases to the set point value as determined by pot P1.

In point of fact, the probe assembly (probe 10, cord 12, connector 13) is tuned approximately to the $f_d$ or driving frequency of the oscillator 41, and this tuning can be effected by adjusting the number of turns in the sensing coil 24. The reason for this is better explained by reference to FIGS. 3 and 4, wherein point A denotes a properly tuned probe assembly (10, 12, 13) and points B and C denote improperly tuned probe assemblies. The number of turns in the coil 24 represented by point A is such that the drop across the coil has a value slightly less than the maximum voltage capable of being produced in the coil by the oscillator circuit, and more importantly, this voltage is on the downside of the voltage-frequency curve (FIG. 3), so that as the coil 24, represented by point A, approaches a metal object, the drop across the coil 24 will steadily decrease.

Each of the probe assemblies represented by points B and C, on the other hand, has too few turns in its probe coil 24, so that when the latter approaches a metallic object the voltage drop across the coil 24 will increase slightly (see arrows in FIG. 3) before decreasing. Assuming that the alarm 50 has been set to be energized when the probe voltage reaches the value indicated by the broken lines in FIGS. 3 and 4 the probe assembly denoted by C would be entirely unsatisfactory because it normally would energize the alarm, and would momentarily deenergize the alarm as the probe coil 24 approached a metallic object.

Figure 4:
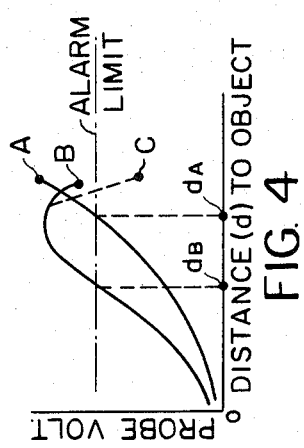

As shown by FIG. 4, the probe assembly denoted by point B likewise would not be satisfactory because it would not be anywhere as near as sensitive as the probe assembly represented by point A. Since the voltage across the assembly denoted by point A steadily drops as its coil 24 approaches a metallic object, it would trigger the alarm 50 at a distance $d_A$ from the object, while the probe coil represented by point B would have to reach the lesser distance $d_B$ before triggering this alarm.

During construction, a probe assembly 10, 12 and 13 can be tuned before fixing the core 23 in tube 22 by attaching the connector 13 to housing 14 before the latter is sealed closed. A high input impedance voltmeter is connected at one side to the juncture of R7, R8 and the drain of Q2, and at its opposite side to ground. The turns of coil 24 are then adjusted (increased or decreased) until the voltage indicated by the meter begins to drop as the probe coil is moved into the vicinity of a metallic object. The pot P1 is then adjusted to set the alarm voltage which will be required across coil 24 in order to energize alarm 50. The voltmeter is then removed, and the housing is closed; the coil 24 is fastened by a glue to the core; and the core and one end of the cable are vacuum potted or otherwise secured in tube 22 with an epoxy resin filler of the type noted above, thereby to seal the core, coil and cable against movement in the tube. This construction causes the probe assembly 10, 12 13 to remain tuned (as at A in FIG. 3) throughout its use.

Figure 3:
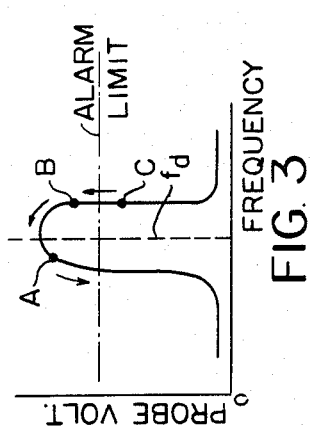
FIGS. 3 and 4 are graphical comparisons of certain characteristics of properly and improperly tuned such devices.

From the foregoing it will be apparent that the present invention provides an extremely compact and reliable probe for detecting metal objects in human and animal bodies. The probe coil 24 is shock excited by the output of the oscillator 41, and unlike most prior art sensing devices, although it generates a sinusoidal wave it is not driven with a sinusoidal wave. The distributed capacitance represented by the fixed length of the probe assembly is connected in parallel with the inductance represented by the coil 24, and together they function as the tank circuit for the oscillator. As a consequence, if the probe assembly 10, 12, 13 is tuned exactly to the oscillator output, the current flow through coil 24 normally will be at a minimum, and the voltage drop thereacross at a maximum, as shown in FIG. 3. However, by pre-tuning the assembly as noted above—i.e., by selecting the number of turns in the coil 24 so that its inductance normally causes the voltage drop across the coil to be slightly less than said maximum (point A in FIG. 3)—it has been possible to produce an extremely sensitive probe, and one which does not require any adjustment prior to its use. The only manual operation required is the manipulation of the ON-OFF switch in order to energize or deenergize the device.

The high input impedance RF amplifier 45 serves to isolate the loading effects of the detector unit 46 from the probe circuit or coil. Likewise, the high input impedance DC amplifier 47 serves to isolate the comparator 48 from the detector unit 46. The probe and detector circuits thus remain stable and produce no change in the output of the comparator 48 until such time that the coil 24 detects the presence of a metallic object. The distance between the coil 24 and the metallic object required to trigger the alarm 50 will, of course, depend to a greater extent upon the overall power supply of the system, and also upon the set point established by the pot P1.

Still another advantage of this probe device is that it is very small and portable. The probe itself, as represented by the phenolic tube 22, need be no larger than the size of a pencil. By sealing the tube 22, with a plastic coating compatible to the human body (e.g., Teflon, nylon, etc.) the tube can be protected from body fluids and solids, and is readily sterilizable by use of a gas sterilization agent, or the like. Moreover, it will be readily apparent to one skilled in the art that by proper selection of the plastic from which the probe is made, it might even be capable of withstanding sterilization by radiation or auto-claving, or may be inexpensive enough to warrant the manufacture of disposable probes. Moreover, although in practice the probe is pretuned as noted above, it would be possible also to connect to line 44 a small, variable capacitor $C_x$, such as shown in phantom by broken lines in FIG. 2, which would be adjustable from the exterior of housing 14 to correct any undesirable detuning that might occur because of temperature changes or replacement of the probe, cable, connector assembly (10, 12, 13).

While this invention has been illustrated and described in detail in connection with only certain embodiments thereof, it will be apparent that it is capable of still further modification, and that this application is intended to cover any such modifications as may fall within the scope of one skilled in the art or the appended claims.

What is claimed is:

1. An electronic anatomical probe device, comprising
   a housing having thereon a manually operable switch movable between ON and OFF positions, respectively,
   a solid state, fixed frequency oscillator secured in said housing, a DC power supply means in said housing for energizing said oscillator when said switch is in its ON position, a tubular probe having a tip end disposed to be inserted in a wound or the like, a wire sensing coil sealed in the tip end of said probe, means connecting said coil to the output of said oscillator, including an elongate, coaxial cable secured at one end in said probe to said coil, and releasably connected at its opposite end to said housing and to the output of said oscillator, said coil and said connecting means being tuned to the frequency of the output of said oscillator, whereby when energized thereby, the voltage drop across said coil remains constant until the coil approaches a metallic object, means in said housing for sensing the voltage drop across said coil, and alarm means connected to said sensing means and operable thereby to provide a warning signal in response to a predetermined change in said voltage drop across said coil.

2. A device as defined in claim 1, including a high impedance resistor connected between said coil and the output of said oscillator to couple said coil to the oscillator output.

3. A device as defined in claim 1, wherein said sensing means comprises a voltage comparator, having at least two inputs and an output connected to said alarm means, adjustable means for applying a first, predetermined DC voltage to one of said inputs, and means for converting the voltage drop in said coil to a DC signal and applying it to the other input of said comparator.

4. A device as defined in claim 1, wherein said DC power supply means comprises a rechargeable battery mounted in said housing with its positive terminal connected to said switch, and a battery charging circuit in said housing disposed to be connected to the positive terminal of said battery when said switch is in its OFF position.

5. A device as defined in claim 4, including a rectifier in said battery charging circuit, and means on said housing for releasably coupling the input of said rectifier to an AC power supply located externally of said housing.

6. A device as defined in claim 4, wherein said alarm means comprises an audible signal generating device mounted in said housing in registry with an opening therein and operative to produce an audible sound when energized by said sensing means.

7. A device as defined in claim 6, including a light emitting element mounted in said housing to be visible from the exterior thereof, when energized, and connected in parallel in said housing with said signal generating device for simultaneous energization therewith.

8. A device as defined in claim 7, including a second light emitting element mounted in said housing to be visible from the exterior thereof, when energized, and connected to said battery charging circuit to be energized thereby when said battery is being recharged.

9. A device as defined in claim 1, including a variable capacitor connected in parallel with said coil to be adjustable from the exterior of said housing.

10. A device as defined in claim 1, wherein said probe comprises a hand manipulable, rigid, plastic tube having a ferrite core secured in its tip end coaxially thereof, said coil is secured around the outside of said core with one end thereof grounded on the shield of said coaxial cable, and with the other end of said coil connected through said cable to the output of said oscillator, and said probe is sealed to permit the sterilization thereof after use.

11. A device for detecting metal objects in a human or animal body, comprising an elongate, slender, hand manipulable probe having a tip at one end disposed to be inserted into a wound or the like in a body, an electrical sensing coil sealed in said tip, a fixed frequency oscillator located externally of said probe, means including an elongate, flexible, coaxial cable operatively connecting the output of said oscillator to said coil, said connecting means and said coil being tuned approximately to the frequency of said oscillator, whereby the voltage drop across said coil remains stable until said coil approaches a metal object, electrical alarm means located externally of said probe, and means connecting said alarm means to said coil and operable to energize said alarm means when a predetermined change in said voltage drop across said coil is caused by placing the tip of said probe near a metallic object, said coil and one end of said cable being sealingly secured against movement in said probe, and the inductance of said coil being selected normally to maintain the voltage drop across said coil at a value slightly less than the maximum value produced thereacross when said connecting means and coil are perfectly tuned to said oscillator.

12. A device as defined in claim 11, wherein said means connecting said alarm means to said coil, comprises signal amplifying means having an input connected between said coil and the output of said oscillator, means comparing the output of said amplifying means with a reference voltage, and means operative to energize said alarm means when the output of said amplifying means differs by a predetermined amount from said reference voltage.

13. A device as defined in claim 12, including manually operable means for adjusting said reference voltage.

14. A device for detecting metal objects in a human or animal body, comprising a housing having mounted therein a fixed frequency oscillator, and a power supply means for energizing said oscillator, a probe assembly including a rigid, tubular probe having a wire sensing coil secured in one end thereof, and an elongate, coaxial cable secured at one end in said probe to said coil, and releasably connected at its opposite end to said housing operatively to couple the output of said oscillator to said coil, said probe assembly being approximately tuned to the frequency of the output of said oscillator, whereby the voltage drop created across said coil by said oscillator output remains substantially constant until said coil approaches a metallic object, and alarm means in said housing connected by said cable to said coil and operative to provide a warning signal when the value of the voltage drop across said coil decreases to a predetermined value below the maximum value capable of being created across said coil by said oscillator output, said coil having an inductance operative normally to cause the voltage drop across said coil to have a value which is less than said maximum value and greater than said predetermined value, and which steadily decreases as said coil approaches a metallic object.

15. A device as defined in claim 14, wherein said alarm means includes adjustable means for presetting said predetermined value of said voltage drop relative to said normal value.

16. A device as defined in claim 14, including a high impedance element connected between said coil and the output of said oscillator to couple the former to the latter.

17. A device as defined in claim 14, wherein said power supply means comprises a rechargeable battery, a manually operable ON-OFF switch is mounted on said housing to connect said power supply means to said oscillator when said switch is in its ON position, and a battery recharging circuit is mounted in said housing automatically to be connected to said battery when said switch is in its OFF position.

18. A device as defined in claim 14, wherein said alarm means comprises a voltage comparator in said housing and having two inputs, means for converting the voltage drop across said coil to a DC signal and applying it to one of said inputs, means for applying a DC voltage of said predetermined value to the other of said inputs, and audible signal means connected to the output of said comparator to be energized when voltage applied to said one input falls below the value of the voltage applied to said other input.

19. A device as defined in claim 18 including a light emitting element connected in parallel with said signal means to be energized therewith, and mounted on said housing to be viewable from the exterior thereof.

20. A device as defined in claim 14, wherein said oscillator is made from solid state components and produces an intermittent square wave signal for driving said coil.

* * * * *